US008039628B2

(12) United States Patent
Porstmann et al.

(10) Patent No.: US 8,039,628 B2
(45) Date of Patent: Oct. 18, 2011

(54) PROCESS FOR PREPARING (ALPHA S, BETA R)-6-BROMO-ALPHA-[2-(DIMETHYLAMINO) ETHYL]-2-METHOXY-ALPHA-1-NAPHTHALENYL-BETA-PHENYL-3-QUINOLINEETHANOL

(75) Inventors: Frank Ralf Porstmann, Schaffhausen (CH); Stefan Horns, Schaffhausen (CH); Thomas Bader, Zürich (CH)

(73) Assignee: Janssen Pharmaceutica N.V., Beerse (BE)

( * ) Notice: Subject to any disclaimer, the term of this patent is extended or adjusted under 35 U.S.C. 154(b) by 595 days.

(21) Appl. No.: 11/915,204

(22) PCT Filed: May 22, 2006

(86) PCT No.: PCT/EP2006/062502
§ 371 (c)(1),
(2), (4) Date: Nov. 21, 2007

(87) PCT Pub. No.: WO2006/125769
PCT Pub. Date: Nov. 30, 2006

(65) Prior Publication Data
US 2008/0200683 A1   Aug. 21, 2008

(30) Foreign Application Priority Data

May 25, 2005   (EP) .................... 05104482

(51) Int. Cl.
C07D 215/00  (2006.01)
C07F 9/02   (2006.01)
(52) U.S. Cl. .......................... 546/157; 558/86
(58) Field of Classification Search .................. 546/157; 558/86
See application file for complete search history.

(56) References Cited

U.S. PATENT DOCUMENTS 5,319,084 A  *  6/1994  Cook et al. .................... 546/111

FOREIGN PATENT DOCUMENTS

| WO | WO 2004/011436 | * | 2/2004 |
| WO | WO 2004/011436 A1 | | 2/2004 |
| WO | WO 2004/060889 A1 | | 7/2004 |

OTHER PUBLICATIONS

Jacques et al. Tetrahedron Letters, 48, 4617-4620, 1971.*
International Search Report dated Oct. 2, 2006 for related International Application No. PCT/EP2006/062502.
Imhof, R. et al., "Design, synthesis, and X-ray data of novel potential antipsychotic agents. Substituted 7-phenylquinolizidines: stereospecific, neuroleptic, and antinociceptive properties.", Journal of Medicinal Chemistry, Feb. 1984, pp. 165-175, vol. 27, No. 2, (XP002373516).
Jacques, J. et al., "Enantiomeric Cyclic Binaphthyl Phosphoric Acids as Resolving Agents", Tetrahedron Letters, 1971, pp. 4617-4620, vol. 48, (XP002373514).
Periasamy M., "Novel Methods of Resolving Raemic Diol and Amino Alcohols", Aldrichimica Acta, Aldrich Chemical Co., Milwaukee, US, 2002, pp. 89-101, vol. 35, No. 3, (XP002373517).
Tamai, Y., et al., "A Practical Method for Resolution of the Optical Isomers of 2,2'-Dihydroxy-1,1'-binaphthalene", 1990, Synthesis, Georg Thieme Verlag, Stuttgart, De, pp. 222-223 (XP002373515).

* cited by examiner

*Primary Examiner* — Nizal Chandrakumar
(74) *Attorney, Agent, or Firm* — Thomas J. Dodd

(57) ABSTRACT

The present invention relates to a process for isolating (αS, βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol by optical resolution with chiral 4-hydroxydinaphtho[2,1-d:1',2'-f][1,3,2]dioxaphosphepin 4-oxide or a derivative thereof, in particular (11bR)-4-hydroxydinaphtho[2,1-d:1',2'-f][1,3,2]dioxaphosphepin 4-oxide, as resolution agent.

1 Claim, No Drawings

PROCESS FOR PREPARING (ALPHA S, BETA R)-6-BROMO-ALPHA-[2-(DIMETHYLAMINO)ETHYL]-2-METHOXY-ALPHA-1-NAPHTHALENYL-BETA-PHENYL-3-QUINOLINEETHANOL

CROSS REFERENCE TO RELATED APPLICATIONS

This application is a national stage application of Patent Application No. PCT/EP2006/062502, filed May 22, 2006, which in turn claims the benefit of EPO Patent Application No. 05104482.4 filed May 25, 2005. The complete disclosures of the aforementioned related patent applications are hereby incorporated herein by reference for all purposes.

The present invention relates to a process for isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol by optical resolution with chiral 4-hydroxydinaphtho[2,1-d:1',2'-f][1,3,2]dioxaphosphepin 4-oxide or derivatives thereof as resolution agent.

6-bromo-α-[2-(dimethylamino)ethyl]-2-methoxy-α-1-naphthalenyl-β-phenyl-3-quinolineethanol and stereoisomeric forms thereof are disclosed in WO 2004/011436 as antimycobacterial agents useful for the treatment of mycobacterial diseases, particularly those diseases caused by pathogenic mycobacteria such as *Mycobacterium (M.) tuberculosis, M. bovis, M. avium* and *M. marinum*.

Enantiomer (αS,βR)-6-bromo-α-[2-(dimethylamino)ethyl]-2-methoxy-α-1-naphthalenyl-β-phenyl-3-quinolineethanol corresponds to compound 12 (or the A1 enantiomer) of WO 2004/011436 and is a preferred compound to treat mycobacterial diseases, in particular tuberculosis. WO 2004/011436 describes its isolation from diastereoisomer A, which corresponds to the racemic mixture of (αS,βR)-6-bromo-α-[2-(dimethylamino)ethyl]-2-methoxy-α-1-naphthalenyl-β-phenyl-3-quinolineethanol (A1 enantiomer) and (αR,βS)-6-bromo-α-[2-(dimethylamino)ethyl]-2-methoxy-α-1-naphthalenyl-β-phenyl-3-quinolineethanol (A2 enantiomer) by chiral chromatography.

In order to ensure supply of (αS,βR)-6-bromo-α-[2-(dimethylamino)ethyl]-2-methoxy-α-1-naphthalenyl-β-phenyl-3-quinolineethanol for development purposes and sales, an efficient synthesis process is required which can be carried out on a large, commercial scale.

Therefore, it is an object of the present invention to provide a process for the preparation (isolation) of (αS,βR)-6-bromo-α-[2-(dimethylamino)ethyl]-2-methoxy-α-1-naphthalenyl-β-phenyl-3-quinolineethanol with a high yield and a high enantiomeric excess and which is suitable for operation on a large, commercial scale.

The present invention relates to a process for isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol by optical resolution.

Several chiral acids were tested as optical resolution agent for resolution of (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol. Optical resolution of (αS,βR)-6-bromo-α-[2-(dimethylamino)ethyl]-2-methoxy-α-1-naphthalenyl-β-phenyl-3-quinolineethanol was found to be not straightforward since either crystallization of the resulting chiral salt did not occur or there was no enantiomeric excess.

Unexpectedly it was found that when using chiral 4-hydroxydinaphtho[2,1-d:1',2'-f][1,3,2]dioxaphosphepin 4-oxide or a derivative thereof as resolution agent, optical resolution of (αS,βR)-6-bromo-α-[2-(dimethylamino)ethyl]-2-methoxy-α-1-naphthalenyl-β-phenyl-3-quinolineethanol, which is a compound with two highly sterically hindered chiral centers next to each other, was successful since crystallisation of chiral salt occurred making isolation or separation of the chiral salt from the reaction mixture possible, and since a high enantiomeric excess could be achieved.

The process of the present invention makes it possible to isolate the desired (αS,βR) enantiomer from a mixture containing all 4 enantiomers. The process also makes it possible to purify the desired (αS,βR) enantiomer from other process impurities.

The term enantiomeric excess (e.e.) is well-known to the person skilled in stereochemistry. For a mixture of (+) and (−) enantiomers, with composition given as the mole or weight fractions of F(+) and F(−) (where F(+)+F(−)=1), the enantiomeric excess for F(+) is defined as F(+)−F(−), and the percent enantiomeric excess as 100*[F(+)−F(−)].

Therefore, the present invention relates to the use of chiral 4-hydroxydinaphtho[2,1-d:1',2'-f][1,3,2]dioxaphosphepin 4-oxide or a derivative thereof as a resolution agent for isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol.

6-bromo-α-[2-(dimethylamino)ethyl]-2-methoxy-α-1-naphthalenyl-β-phenyl-3-quinolineethanol is a compound of formula

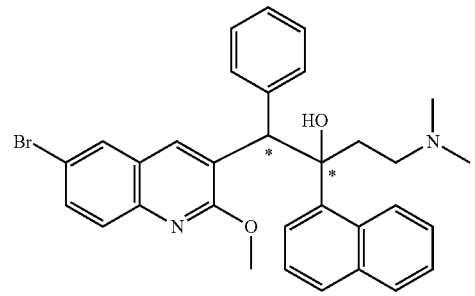

and has two chiral centra indicated by * in the formula. It exists as 4 stereoisomeric forms, i.e. (αS,βR)-6-bromo-α-[2-(dimethylamino)ethyl]-2-methoxy-α-1-naphthalenyl-β-phenyl-3-quinolineethanol, (αR,βS)-6-bromo-α-[2-(dimethylamino)ethyl]-2-methoxy-α-1-naphthalenyl-β-phenyl-3-quinolineethanol, (αR,βR)-6-bromo-α-[2-(dimethylamino)ethyl]-2-methoxy-α-1-naphthalenyl-β-phenyl-3-quinolineethanol and (αS,βS)-6-bromo-α-[2-(dimethylamino)ethyl]-2-methoxy-α-1-naphthalenyl-β-phenyl-3-quinolineethanol. The 4 stereoisomeric forms can be present under the form of 2 diastereoisomers, i.e. a racemic mixture of (αS,βR)-6-bromo-α-[2-(dimethylamino)ethyl]-2-methoxy-α-1-naphthalenyl-β-phenyl-3-quinolineethanol and (αR,βS)-6-bromo-α-[2-(dimethylamino)ethyl]-2-methoxy-α-1-naphthalenyl-β-phenyl-3-quinolineethanol, hereinafter referred to as diastereoisomer A, and a racemic mixture of (αR,βR)-6-bromo-α-[2-(dimethylamino)ethyl]-2-methoxy-α-1-naphthalenyl-β-phenyl-3-quinolineethanol and (αS,βS)-6-bromo-α-[2-(dimethylamino)ethyl]-2-methoxy-α-1-naphthalenyl-β-phenyl-3-quinolineethanol, hereinafter referred to as diastereoisomer B.

Thus, whenever hereinabove or hereinafter, reference is made to a mixture of stereoisomeric forms of 6-bromo-α-[2-(dimethylamino)ethyl]-2-methoxy-α-1-naphthalenyl-β-phenyl-3-quinolineethanol, it means a mixture of the 4 possible stereoisomeric forms, i.e. (αS,βR)-6-bromo-α-[2-(dimethylamino)ethyl]-2-methoxy-α-1-naphthalenyl-β-phenyl-3-quinolineethanol, (αR,βS)-6-bromo-α-[2-(dimethylamino)ethyl]-2-methoxy-α-1-naphthalenyl-β-phenyl-3-quinolineethanol, (αR,βR)-6-bromo-α-[2-(dimethylamino)ethyl]-2-methoxy-α-1-naphthalenyl-β-phenyl-3-quinolineethanol and (αS,βS)-6-bromo-α-[2-(dimethylamino)ethyl]-2-methoxy-α-1-naphthalenyl-β-phenyl-3-quinolineethanol. Preferably, it means a mixture wherein diastereoisomer A is predominantly present, i.e. a mixture containing more than 50%, in particular 80% or more, more in particular 85% or more, or 90% or more of diastereoisomer A or it means diastereoisomer A. Diastereoiosmer A is the racemic mixture which is substantially free of the B diastereoisomer. Substantially free in this context means associated with less than 5%, preferably less than 2%, more preferably less than 1% of the other diastereoisomer or which is essentially pure.

A mixture wherein diastereoisomer A is predominantly present can be obtained by selectively crystallizing diastereoisomer B from a mixture of the A and B diastereoisomers. This can be achieved by seeding the mixture of the A and B diastereoisomers with diastereoisomer B thereby promoting crystallization of diastereoisomer B, which can subsequently be removed from the mixture, for instance by filtration, resulting in a mixture wherein diastereoisomer A is predominantly present.

Diastereoisomer A (substantially free of the B diastereoisomer) can be obtained from the mixture of the A and B diastereoisomers by column chromatography and crystallization (reference therefore is made to WO2004/011436, Example B7).

Whenever used hereinbefore or hereinafter, chiral 4-hydroxydinaphtho[2,1-d:1',2'-f][1,3,2]dioxaphosphepin 4-oxide or a derivative thereof means chiral 4-hydroxydinaphtho[2,1-d:1',2'-f][1,3,2]dioxaphosphepin 4-oxide or chiral 4-hydroxydinaphtho[2,1-d:1',2'-f][1,3,2]dioxaphosphepin 4-oxide wherein one or both of the naphthyl rings are substituted with one or more substituents.

In particular, chiral 4-hydroxydinaphtho[2,1-d:1',2'-f][1,3,2]dioxaphosphepin 4-oxide or a derivative thereof represents a chiral compound of formula (I)

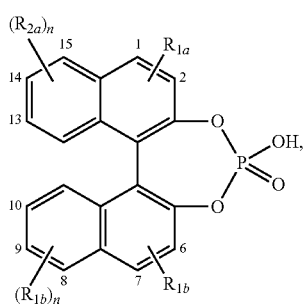

(I)

wherein
n is an integer equal to 1 or 2;
$R_{1a}$ and $R_{1b}$ each independently represent hydrogen; halo; $C_{1-12}$alkyl optionally substituted with aryl; aryl; naphthyl; Si(phenyl)$_3$; $C_{1-6}$alkyloxy; antracenyl; $C_{2-6}$alkynyl optionally substituted with aryl;
$R_{2a}$ and $R_{2b}$ each independently represent hydrogen; halo; $C_{1-12}$alkyl optionally substituted with aryl; aryl; $C_{2-12}$alkenyl; $C_{1-6}$alkyloxy optionally substituted with phenyl; nitro; hydroxy;
$R_{2a}$ in position 14 and in position 15 of the 4-hydroxydinaphtho[2,1-d:1',2'-f][1,3,2]dioxaphosphepin 4-oxide may also be taken together to form together with the naphthyl ring to which both $R_{2a}$ substituents are attached 13-methyl-12,13,14,15,16,17-hexahydro-11H-cyclopenta[a]phenanthrene;
$R_{2b}$ in position 8 and in position 9 of the 4-hydroxydinaphtho[2,1-d:1',2'-f][1,3,2]dioxaphosphepin 4-oxide may also be taken together to form together with the naphthyl ring to which both $R_{2b}$ substituents are attached 13-methyl-12,13,14,15,16,17-hexahydro-11H-cyclopenta[a]phenanthrene;
aryl is phenyl or phenyl substituted with one, two or three substituents each independently selected from $C_{1-6}$alkyl, polyhalo$C_{1-6}$alkyl, $C_{1-6}$alkyloxy substituted with phenyl, phenyl optionally substituted with one, two or three substituents selected from $C_{1-6}$alkyl or naphthyl.

Interesting embodiments of the compounds of formula (I) are compounds wherein one or where possible more of the following conditions apply:
Preferably the $R_{1a}$ substituent is placed in position 1 or 2 of the 4-hydroxydinaphtho[2,1-d:1',2'-f][1,3,2]dioxaphosphepin 4-oxide.
Preferably, the $R_{1b}$ substituent is placed in position 6 or 7 of the 4-hydroxydinaphtho[2,1-d:1',2'-f][1,3,2]dioxaphosphepin 4-oxide.
Preferably, the $R_{2a}$ substituent is placed in position 14 or 15 of the 4-hydroxydinaphtho[2,1-d:1',2'-f][1,3,2]dioxaphosphepin 4-oxide.
Preferably, the $R_{2b}$ substituent is placed in position 8 or 9 of the 4-hydroxydinaphtho[2,1-d:1',2'-f][1,3,2]dioxaphosphepin 4-oxide.
Preferably, the $R_{2a}$ substituent is placed in position 13 and 14 of the 4-hydroxydinaphtho[2,1-d:1',2'-f][1,3,2]dioxaphosphepin 4-oxide.
Preferably, the $R_{2b}$ substituent is placed in position 9 and 10 of the 4-hydroxydinaphtho[2,1-d:1',2'-f][1,3,2]dioxaphosphepin 4-oxide.
Chiral 4-hydroxydinaphtho[2,1-d:1',2'-f][1,3,2]dioxaphosphepin 4-oxide or a derivative thereof or the chiral compounds of formula (I) comprise:
(11bR)-4-hydroxy-2,6-bis[2,4,6-tris(1-methylethyl)phenyl]dinaphtho-[2,1-d:1',2'-f][1,3,2]dioxaphosphepin 4-oxide;
(11bR)-2,6-bis[3,5-bis(trifluoromethyl)phenyl]-4-hydroxydinaphtho-[2,1-d:1',2'-f][1,3,2]dioxaphosphepin 4-oxide;
(11bR)-9,14-dibromo-4-hydroxy-2,6-diphenyldinaphtho[2,1-d:1',2'-f]-[1,3,2]dioxaphosphepin 4-oxide;
(11bR)-4-hydroxy-2,6-bis(2',4',6'-trimethyl[1,1'-biphenyl]-4-yl)dinaphtho-[2,1-d:1',2'-f][1,3,2]dioxaphosphepin 4-oxide;
(11bR)-4-hydroxy-2,6-di-2-naphthalenyldinaphtho[2,1-d:1',2'-f][1,3,2]-dioxaphosphepin 4-oxide;
(11bR)-4-hydroxy-2,6-bis(triphenylsilyl)dinaphtho[2,1-d:1',2'-f][1,3,2]-dioxaphosphepin 4-oxide;
(11bR)-2,6-bis(2,2'',4,4'',6,6''-hexamethyl[1,1':3',1''-terphenyl]-5'-yl)-4-hydroxy-dinaphtho[2,1-d:1',2'-f][1,3,2]dioxaphosphepin 4-oxide;
(11bR)-4-hydroxy-2,6-bis[4-(2-naphthalenyl)phenyl]dinaphtho[2,1-d:1',2'-f]-[1,3,2]dioxaphosphepin 4-oxide;

(11bR)-4-hydroxy-2,6-bis(2,4,6-trimethylphenyl)dinaphtho[2,1-d:1',2'-f]-[1,3,2]dioxaphosphepin 4-oxide;
(11bR)-4-hydroxy-2,6-diphenyldinaphtho[2,1-d:1',2'-f][1,3,2]dioxaphosphepin 4-oxide;
(11bS)-4-hydroxy-1,7,9,14-tetraoctyldinaphtho[2,1-d:1',2'-f][1,3,2]-dioxaphosphepin 4-oxide;
(11bS)-4-hydroxy-1,7,9,14-tetrakis(2-phenylethyl)dinaphtho[2,1-d:1',2'-f]-[1,3,2]dioxaphosphepin 4-oxide;
(11bS)-1,7,9,14-tetrakis(4-butylphenyl)-4-hydroxydinaphtho[2,1-d:1',2'-f]-[1,3,2]dioxaphosphepin 4-oxide;
(11bS)-4-hydroxy-1,7,9,14-tetraphenyldinaphtho[2,1-d:1',2'-f]-[1,3,2]-dioxaphosphepin 4-oxide;
(4S,14β)-(14'β)[4,4'-Biestra-1,3,5,7,9-pentaene]-3,3'-diol, cyclic hydrogen phosphate;
(4R,14β)-(14'β)[4,4'-Biestra-1,3,5,7,9-pentaene]-3,3'-diol, cyclic hydrogen phosphate;
(11bR)-9,14-dibromo-4-hydroxydinaphtho[2,1-d:1',2'-f][1,3,2]dioxaphosphepin 4-oxide;
(11bR)-4-hydroxy-2,6-bis([1,1':3',1''-terphenyl]-5'-yl)dinaphtho[2,1-d:1',2'-f]-[1,3,2]dioxaphosphepin 4-oxide;
(11bS)-2,6-di-9-anthracenyl-4-hydroxydinaphtho[2,1-d:1',2'-f][1,3,2]dioxaphosphepin 4-oxide;
(11bR)-2,6-di-9-anthracenyl-4-hydroxydinaphtho[2,1-d:1',2'-f][1,3,2]-dioxaphosphepin 4-oxide;
(11bR)-2,6-diethynyl-4-hydroxydinaphtho[2,1-d:1',2'-f][1,3,2]dioxaphosphepin 4-oxide;
(11bR)-9,14-bis(2,6-dimethylphenyl)-4-hydroxydinaphtho[2,1-d:1',2'-f]-[1,3,2]dioxaphosphepin 4-oxide;
(11bR)-4-hydroxy-9,14-dioctyldinaphtho[2,1-d:1',2'-f][1,3,2]dioxaphosphepin 4-oxide;
(R)-9,14-dibromo-4-hydroxy-10,13-bis(phenylmethoxy)dinaphtho[2,1-d:1',2'-f]-[1,3,2]dioxaphosphepin 4-oxide;
(S)-9,14-dibromo-4-hydroxy-10,13-bis(phenylmethoxy)dinaphtho[2,1-d:1',2'-f]-[1,3,2]dioxaphosphepin 4-oxide;
4-hydroxy-10,13-bis(phenylmethoxy)dinaphtho[2,1-d:1',2'-f][1,3,2]-dioxaphosphepin 4-oxide;
(S)-4-hydroxy-10,13-bis(phenylmethoxy)dinaphtho[2,1-d:1',2'-f][1,3,2]dioxaphosphepin 4-oxide;
(R)-4-hydroxy-10,13-dimethoxydinaphtho[2,1-d:1',2'-f][1,3,2]dioxaphosphepin 4-oxide;
(R)-4-hydroxydinaphtho[2,1-d:1',2'-f][1,3,2]dioxaphosphepin-10,13-diol 4-oxide;
(R)-4-hydroxy-10,13-bis(phenylmethoxy)dinaphtho[2,1-d:1',2'-f][1,3,2]dioxaphosphepin 4-oxide;
(R)-4-hydroxy-2,6-dimethyldinaphtho[2,1-d:1',2'-f][1,3,2]dioxaphosphepin 4-oxide;
(S)-4-hydroxy-2,6-dimethyldinaphtho[2,1-d:1',2'-f][1,3,2]dioxaphosphepin 4-oxide;
(11bR)-4-hydroxydinaphtho[2,1-d:1',2'-f][1,3,2]dioxaphosphepin 4-oxide;
(11bS)-4-hydroxydinaphtho[2,1-d:1',2'-f][1,3,2]dioxaphosphepin 4-oxide.

Preferably, the resolution agent is (11bR)-4-hydroxydinaphtho[2,1-d:1',2'-f][1,3,2]dioxaphosphepin 4-oxide or (11bS)-4-hydroxydinaphtho[2,1-d:1',2'-f][1,3,2]dioxaphosphepin 4-oxide.

Most preferably, the resolution agent is (11bR)-4-hydroxydinaphtho[2,1-d:1',2'-f][1,3,2]dioxaphosphepin 4-oxide.

As used hereinbefore or hereinafter $C_{1-6}$alkyl as a group or part of a group defines straight or branched chain saturated hydrocarbon radicals having from 1 to 6 carbon atoms such as methyl, ethyl, propyl, 1-methylethyl, butyl, pentyl, hexyl, 2-methylbutyl and the like; $C_{1-12}$alkyl as a group or part of a group defines straight or branched chain saturated hydrocarbon radicals having from 1 to 12 carbon atoms such as the group defined for $C_{1-6}$alkyl and heptyl, octyl, nonyl, decyl and the like; $C_{2-12}$alkenyl defines straight and branched chain hydrocarbon radicals having from 2 to 12 carbon atoms containing a double bond such as ethenyl, propenyl, butenyl, pentenyl, hexenyl, methyleneoctyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like.

The term halo is generic to fluoro, chloro, bromo and iodo. As used hereinbefore or hereinafter, polyhalo$C_{1-6}$alkyl as a group or part of a group is defined as mono- or polyhalosubstituted $C_{1-6}$alkyl, for example methyl with one or more fluoro atoms, for example, difluoromethyl or trifluoromethyl, 1,1-difluoro-ethyl and the like. In case more than one halogen atoms are attached to an alkyl group within the definition of polyhalo$C_{1-6}$alkyl, they may be the same or different.

The compound of formula (I) may also be used in hydrate form or solvent addition form which the compound of formula (I) is able to form. Examples of such forms are e.g. hydrates, alcoholates and the like.

The present process to isolate (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol by optical resolution with chiral 4-hydroxydinaphtho[2,1-d:1',2'-f][1,3,2]dioxaphosphepin 4-oxide or a derivative thereof as resolution agent encompasses two embodiments.

In a first embodiment, the salt of the desired (αS,βR) enantiomer and the resolution agent crystallizes.

In a second embodiment, the salt of the (αR,βS) enantiomer and the resolution agent crystallizes.

These two embodiments will be described hereinafter in more detail.

FIRST EMBODIMENT

The invention relates to a process for isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol by optical resolution with chiral 4-hydroxydinaphtho[2,1-d:1',2'-f][1,3,2]dioxaphosphepin 4-oxide or a derivative thereof as resolution agent, wherein the salt of (αS,βR)-6-bromo-α-[2-(dimethylamino)ethyl]-2-methoxy-α-1-naphthalenyl-β-phenyl-3-quinolineethanol and the resolution agent crystallizes.

The present invention further relates to a process for isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol by optical resolution with chiral 4-hydroxydinaphtho[2,1-d:1',2'-f][1,3,2]dioxaphosphepin 4-oxide or a derivative thereof as resolution agent, wherein the salt of (αS,βR)-6-bromo-α-[2-(dimethylamino)ethyl]-2-methoxy-α-1-naphthalenyl-β-phenyl-3-quinolineethanol and the resolution agent crystallizes, said process comprising
a) reacting a mixture of stereoisomeric forms of 6-bromo-α-[2-(dimethylamino)ethyl]-2-methoxy-α-1-naphthalenyl-β-phenyl-3-quinolineethanol with said resolution agent in a suitable solvent;
b) separating the resulting salt of (αS,βR)-6-bromo-α-[2-(dimethylamino)ethyl]-2-methoxy-α-1-naphthalenyl-β-phenyl-3-quinolineethanol and said resolution agent from the reaction mixture obtained under a);
c) optionally recrystallizing or slurry the salt obtained under b) in a suitable solvent;

d) liberating (αS,βR)-6-bromo-α-[2-(dimethylamino)ethyl]-2-methoxy-α-1-naphthalenyl-β-phenyl-3-quinolineethanol from the salt obtained under b) or c).

Since (11bR)-4-hydroxydinaphtho[2,1-d:1',2'-f][1,3,2]dioxaphosphepin 4-oxide is a preferred resolution agent, the present invention also relates to a process for isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol by optical resolution with (11bR)-4-hydroxydinaphtho[2,1-d:1',2'-f][1,3,2]dioxaphosphepin 4-oxide as resolution agent, wherein the salt of (αS,βR)-6-bromo-α-[2-(dimethylamino)ethyl]-2-methoxy-α-1-naphthalenyl-β-phenyl-3-quinolineethanol and the resolution agent crystallizes, said process comprising a) reacting a mixture of stereoisomeric forms of 6-bromo-α-[2-(dimethylamino)ethyl]-2-methoxy-α-1-naphthalenyl-β-phenyl-3-quinolineethanol with (11bR)-4-hydroxydinaphtho[2,1-d:1',2'-f][1,3,2]dioxaphosphepin 4-oxide in a suitable solvent;

b) separating the resulting (αS,βR)-6-bromo-α-[2-(dimethylamino)ethyl]-2-methoxy-α-1-naphthalenyl-β-phenyl-3-quinolineethanol * (11bR)-4-hydroxydinaphtho[2,1-d:1',2'-f][1,3,2]dioxaphosphepin 4-oxide salt from the reaction mixture obtained under a);

c) optionally recrystallizing or slurry the salt obtained under b) in a suitable solvent;

d) liberating (αS,βR)-6-bromo-α-[2-(dimethylamino)ethyl]-2-methoxy-α-1-naphthalenyl-β-phenyl-3-quinolineethanol from the salt obtained under b) or c).

As the salt of (αS,βR)-6-bromo-α-[2-(dimethylamino)ethyl]-2-methoxy-α-1-naphthalenyl-β-phenyl-3-quinolineethanol and the resolution agent crystallizes in the above described processes, it can be separated from the reaction mixture by for instance filtration.

The solvent under a) may also be a mixture of different solvents. In a preferred embodiment of the present invention the suitable solvent under a) is a ketone, an ester, a mixture of a ketone with an aprotonic polar solvent, or a mixture of an ester with an aprotonic polar solvent. Preferably the ketone is acetone or methyl ethylketone. Preferably, the ester is ethyl acetate or butyl acetate, more preferably butyl acetate. The aprotonic polar solvent for the mixture with the ketone is preferably dimethylsulfoxide, N,N-dimethylformamide, N,N-dimethylacetamide or N-methylpyrrolidone. The aprotonic polar solvent for the mixture with the ester, preferably butyl acetate, is preferably dimethylsulfoxide or N,N-dimethylformamide, preferably dimethylsulfoxide. Preferably, the solvent under a) is a ketone or a mixture of a ketone with an aprotonic polar solvent. More preferably, the solvent under a) is acetone, or the solvent under a) is a mixture of acetone with dimethylsulfoxide or N,N-dimethylformamide, in particular a mixture of acetone and dimethylsulfoxide.

In a preferred embodiment of the present invention, the amount of chiral 4-hydroxydinaphtho[2,1-d:1',2'-f][1,3,2]dioxaphosphepin 4-oxide or a derivative thereof, in particular (11bR)-4-hydroxydinaphtho[2,1-d:1',2'-f][1,3,2]dioxaphosphepin 4-oxide, ranges from 0.5 to 1.5 equivalents, preferably from 0.8 to 1.2 equivalents, most preferably is 1 equivalent, calculated on the sum of diastereoisomers A and B present in the mixture under a), i.e. calculated on the sum of stereoisomeric forms of 6-bromo-α-[2-(dimethylamino)ethyl]-2-methoxy-α-1-naphthalenyl-β-phenyl-3-quinolineethanol present in the mixture under a).

In a preferred embodiment of the present invention, the reaction mixture under a) is seeded with seeds of the salt of (αS,βR)-6-bromo-α-[2-(dimethylamino)ethyl]-2-methoxy-α-1-naphthalenyl-β-phenyl-3-quinolineethanol and chiral 4-hydroxydinaphtho[2,1-d:1',2'-f][1,3,2]dioxaphosphepin 4-oxide or a derivative thereof, in particular with seeds of (αS,βR)-6-bromo-α-[2-(dimethylamino)ethyl]-2-methoxy-α-1-naphthalenyl-β-phenyl-3-quinolineethanol * (11bR)-4-hydroxydinaphtho[2,1-d:1',2'-f][1,3,2]dioxaphosphepin 4-oxide salt, before adding chiral 4-hydroxydinaphtho[2,1-d:1',2'-f][1,3,2]dioxaphosphepin 4-oxide or a derivative thereof, in particular (11bR)-4-hydroxydinaphtho[2,1-d:1',2'-f][1,3,2]dioxaphosphepin 4-oxide, to the reaction mixture.

In another preferred embodiment of the present invention, the reaction mixture under a) is seeded with seeds of the salt of (αS,βR)-6-bromo-α-[2-(dimethylamino)ethyl]-2-methoxy-α-1-naphthalenyl-β-phenyl-3-quinolineethanol and chiral 4-hydroxydinaphtho[2,1-d:1',2'-f][1,3,2]dioxaphosphepin 4-oxide or a derivative thereof, in particular with seeds of (αS,βR)-6-bromo-α-[2-(dimethylamino)ethyl]-2-methoxy-α-1-naphthalenyl-β-phenyl-3-quinolineethanol * (11bR)-4-hydroxydinaphtho[2,1-d:1',2'-f][1,3,2]dioxaphosphepin 4-oxide salt, after adding chiral 4-hydroxydinaphtho[2,1-d:1',2'-f][1,3,2]dioxaphosphepin 4-oxide or a derivative thereof, in particular (11bR)-4-hydroxydinaphtho[2,1-d:1',2'-f][1,3,2]dioxaphosphepin 4-oxide, to the reaction mixture.

More preferably, the reaction mixture under a) is seeded with seeds of the salt of (αS,βR)-6-bromo-α-[2-(dimethylamino)ethyl]-2-methoxy-α-1-naphthalenyl-β-phenyl-3-quinolineethanol and chiral 4-hydroxydinaphtho[2,1-d:1',2'-f][1,3,2]dioxaphosphepin 4-oxide or a derivative thereof, in particular with seeds of (αS,βR)-6-bromo-α-[2-(dimethylamino)ethyl]-2-methoxy-α-1-naphthalenyl-β-phenyl-3-quinolineethanol * (11bR)-4-hydroxydinaphtho[2,1-d:1',2'-f][1,3,2]dioxaphosphepin 4-oxide salt, before and after adding chiral 4-hydroxydinaphtho[2,1-d:1',2'-f][1,3,2]dioxaphosphepin 4-oxide or a derivative thereof, in particular (11bR)-4-hydroxydinaphtho[2,1-d:1',2'-f][1,3,2]dioxaphosphepin 4-oxide, to the reaction mixture.

By adding seeds of the chiral salt to the reaction mixture under a), the enantiomeric excess and the filterability of the resulting solid is improved.

Seeds of salt of (αS,βR)-6-bromo-α-[2-(dimethylamino)ethyl]-2-methoxy-α-1-naphthalenyl-β-phenyl-3-quinolineethanol and chiral 4-hydroxydinaphtho[2,1-d:1',2'-f][1,3,2]dioxaphosphepin 4-oxide or a derivative thereof, in particular seeds of (αS,βR)-6-bromo-α-[2-(dimethylamino)ethyl]-2-methoxy-α-1-naphthalenyl-β-phenyl-3-quinolineethanol * (11bR)-4-hydroxydinaphtho[2,1-d:1',2'-f][1,3,2]dioxaphosphepin 4-oxide salt, can be obtained from previously performed processes for the preparation of (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol by using chiral 4-hydroxydinaphtho[2,1-d:1',2'-f][1,3,2]dioxaphosphepin 4-oxide or a derivative thereof, in particular (11bR)-4-hydroxydinaphtho[2,1-d:1',2'-f][1,3,2]dioxaphosphepin 4-oxide, as the resolution agent, such as the process subject of the present invention.

In a preferred embodiment of the present invention chiral 4-hydroxydinaphtho[2,1-d:1',2'-f][1,3,2]dioxaphosphepin 4-oxide or a derivative thereof, in particular (11bR)-4-hydroxydinaphtho[2,1-d:1',2'-f][1,3,2]dioxaphosphepin 4-oxide, is added to the mixture of stereoisomeric forms of 6-bromo-α-[2-(dimethylamino)ethyl]-2-methoxy-α-1-naphthalenyl-β-phenyl-3-quinolineethanol as a solution in a suitable solvent. Said solvent is preferably an aprotonic polar solvent, such as for example dimethylsulfoxide, N,N-dimethylformamide, N,N-dimethylacetamide or N-methylpyrrolidone, more preferably the aprotic polar solvent is dimethylsulfoxide or N,N-dimethylformamide, most preferred is dimethylsulfoxide.

By adding chiral 4-hydroxydinaphtho[2,1-d:1',2'-f][1,3,2]dioxaphosphepin 4-oxide or a derivative thereof, in particular (11bR)-4-hydroxydinaphtho[2,1-d:1',2'-f][1,3,2]dioxaphosphepin 4-oxide, to the reaction mixture under a) as a solution, the efficiency of the reaction and handling of the reagents is increased.

In a preferred embodiment, the mixture of stereoisomeric forms of 6-bromo-α-[2-(dimethylamino)ethyl]-2-methoxy-α-1-naphthalenyl-β-phenyl-3-quinolineethanol under a) of the above-described processes is a mixture wherein diastereoisomer A is predominantly present.

In a preferred embodiment of the present invention, recrystallization and or slurry of the obtained salt of (αS,βR)-6-bromo-α-[2-(dimethylamino)ethyl]-2-methoxy-α-1-naphthalenyl-β-phenyl-3-quinolineethanol and chiral 4-hydroxydinaphtho[2,1-d:1',2'-f][1,3,2]dioxaphosphepin 4-oxide or a derivative thereof, in particular of the (αS,βR)-6-bromo-α-[2-(dimethylamino)ethyl]-2-methoxy-α-1-naphthalenyl-β-phenyl-3-quinolineethanol * (11bR)-4-hydroxydinaphtho[2,1-d:1',2'-f][1,3,2]dioxaphosphepin 4-oxide salt, is performed before the desired base is liberated from the chiral salt, to increase the ee and chemical purity. The recrystallization or slurry is performed in a suitable solvent, such as for example acetone, N,N-dimethylformamide, a N,N-dimethylformamide/water mixture, a dimethylsulfoxide/water mixture, a dimethylsulfoxide/acetone mixture, a dimethylsulfoxide/alcohol mixture or a N,N-dimethylformamide/alcohol mixture. Preferably, the recrystallization is performed in acetone.

In a preferred embodiment of the present invention, (αS,βR)-6-bromo-α-[2-(dimethylamino)ethyl]-2-methoxy-α-1-naphthalenyl-β-phenyl-3-quinolineethanol is liberated from the salt of (αS,βR)-6-bromo-α-[2-(dimethylamino)ethyl]-2-methoxy-α-1-naphthalenyl-β-phenyl-3-quinolineethanol and chiral 4-hydroxydinaphtho[2,1-d:1',2'-f][1,3,2]dioxaphosphepin 4-oxide or a derivative thereof, in particular from the (αS,βR)-6-bromo-α-[2-(dimethylamino)ethyl]-2-methoxy-α-1-naphthalenyl-β-phenyl-3-quinolineethanol * (11bR)-4-hydroxydinaphtho[2,1-d:1',2'-f][1,3,2]dioxaphosphepin 4-oxide salt, by reacting the salt in a suitable solvent with a suitable base. Preferably, the solvent is an organic solvent which is immiscible with water or aqueous salt solutions, such as for example toluene or tetrahydrofuran. More preferably, the solvent is toluene.

In a preferred embodiment of the present invention the base used to liberate (αS,βR)-6-bromo-α-[2-(dimethylamino)ethyl]-2-methoxy-α-1-naphthalenyl-β-phenyl-3-quinolineethanol from the above described salt is a carbonate base or a phosphate base.

Preferably, the base is $K_2CO_3$, $KHCO_3$, $Na_2CO_3$, $NaHCO_3$, $Na_3PO_4$ or $Na_2HPO_4$. More preferably, the base is $K_2CO_3$.

In order to increase the purity, the obtained (αS,βR) enantiomer can be further recrystallized in a suitable solvent, for instance ethanol or toluene, as is described hereinafter.

The present invention also relates to the salt of (αS,βR)-6-bromo-α-[2-(dimethylamino)ethyl]-2-methoxy-α-1-naphthalenyl-β-phenyl-3-quinolineethanol and chiral 4-hydroxydinaphtho[2,1-d:1',2'-f][1,3,2]dioxaphosphepin 4-oxide or a derivative thereof, in particular to the (αS,βR)-6-bromo-α-[2-(dimethylamino)ethyl]-2-methoxy-α-1-naphthalenyl-β-phenyl-3-quinolineethanol * (11bR)-4-hydroxydinaphtho[2,1-d:1',2'-f][1,3,2]dioxaphosphepin 4-oxide salt.

SECOND EMBODIMENT

As already indicated hereinabove, an alternative way of isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol by optical resolution with chiral 4-hydroxydinaphtho[2,1-d:1',2'-f][1,3,2]dioxaphosphepin 4-oxide or a derivative thereof as resolution agent according to the present invention is a process wherein the salt of (αR,βS)-6-bromo-α-[2-(dimethylamino)ethyl]-2-methoxy-α-1-naphthalenyl-β-phenyl-3-quinolineethanol and the resolution agent crystallizes.

Therefore, the present invention also relates to a process for isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol by optical resolution with chiral 4-hydroxydinaphtho[2,1-d:1',2'-f][1,3,2]dioxaphosphepin 4-oxide or a derivative thereof as resolution agent, wherein the salt of (αR,βS)-6-bromo-α-[2-(dimethylamino)ethyl]-2-methoxy-α-1-naphthalenyl-β-phenyl-3-quinolineethanol and the resolution agent crystallizes, said process comprising
a) reacting a mixture of stereoisomeric forms of 6-bromo-α-[2-(dimethylamino)ethyl]-2-methoxy-α-1-naphthalenyl-β-phenyl-3-quinolineethanol with said resolution agent in a suitable solvent;
b) separating the resulting salt of (αR,βS)-6-bromo-α-[2-(dimethylamino)ethyl]-2-methoxy-α-1-naphthalenyl-β-phenyl-3-quinolineethanol and said resolution agent from the reaction mixture obtained under a);
c) isolating (αS,βR)-6-bromo-α-[2-(dimethylamino)ethyl]-2-methoxy-α-1-naphthalenyl-β-phenyl-3-quinolineethanol from the residual mother liquid obtained after separating the resulting salt from the reaction mixture.

For this alternative process, (11bS)-4-hydroxydinaphtho[2,1-d:1',2'-f][1,3,2]dioxaphosphepin 4-oxide is a preferred resolution agent and therefore the present invention also relates to a process for isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol by optical resolution with (11bS)-4-hydroxydinaphtho[2,1-d:1',2'-f][1,3,2]dioxaphosphepin 4-oxide as resolution agent, wherein the salt of (αR,βS)-6-bromo-α-[2-(dimethylamino)ethyl]-2-methoxy-α-1-naphthalenyl-β-phenyl-3-quinolineethanol and the resolution agent crystallizes, said process comprising
a) reacting a mixture of stereoisomeric forms of 6-bromo-α-[2-(dimethylamino)ethyl]-2-methoxy-α-1-naphthalenyl-β-phenyl-3-quinolineethanol with said resolution agent in a suitable solvent;
b) separating the resulting salt of (αR,βS)-6-bromo-α-[2-(dimethylamino)ethyl]-2-methoxy-α-1-naphthalenyl-β-phenyl-3-quinolineethanol and said resolution agent from the reaction mixture obtained under a);
c) isolating (αS,βR)-6-bromo-α-[2-(dimethylamino)ethyl]-2-methoxy-α-1-naphthalenyl-β-phenyl-3-quinolineethanol from the residual mother liquid obtained after separating the resulting salt from the reaction mixture.

In the alternative processes described above, preferred embodiments of the solvent used under a) and the amount of resolution agent, in particular (11bS)-4-hydroxydinaphtho[2,1-d:1',2'-f][1,3,2]dioxaphosphepin 4-oxide, are comparable with what is described hereinabove for the first embodiment.

Thus, all the above described preferred embodiments for solvent under a) and amount of resolution agent, also apply for the second embodiment.

Also the seeding procedure described hereinabove for the first embodiment applies for the second embodiment, meaning that preferred embodiments of the alternative process encompasses a process wherein the reaction mixture under a) is seeded with seeds of the salt of (αR,βS)-6-bromo-α-[2-(dimethylamino)ethyl]-2-methoxy-α-1-naphthalenyl-β-phenyl-3-quinolineethanol and chiral 4-hydroxydinaphtho[2,1-d:1',2'-f][1,3,2]dioxaphosphepin 4-oxide or a derivative thereof, in particular with seeds of (αR,βS)-6-bromo-α-[2-(dimethylamino)ethyl]-2-methoxy-α-1-naphthalenyl-β-phenyl-3-quinolineethanol * (11bS)-4-hydroxydinaphtho[2,1-d:1',2'-f][1,3,2]dioxaphosphepin 4-oxide salt. The seeds can be added before adding the resolution agent to the reaction mixture, after adding the resolution agent to the reaction mixture or preferably before and after adding the resolution agent to the reaction mixture, in analogy with what is described for the first embodiment.

Seeds of the salt of (αR,βS)-6-bromo-α-[2-(dimethylamino)ethyl]-2-methoxy-α-1-naphthalenyl-β-phenyl-3-quinolineethanol and chiral 4-hydroxydinaphtho[2,1-d:1',2'-f][1,3,2]dioxaphosphepin 4-oxide or a derivative thereof, in particular seeds of (αR,βS)-6-bromo-α-[2-(dimethylamino)ethyl]-2-methoxy-α-1-naphthalenyl-β-phenyl-3-quinolineethanol * (11bS)-4-hydroxydinaphtho[2,1-d:1',2'-f][1,3,2]dioxaphosphepin 4-oxide salt, can be obtained from previously performed processes according to the second embodiment.

For the second embodiment, it is also preferred to add the resolution agent to the reaction mixture as a solution. The same solvents as described hereinabove for the first embodiment can also be used for the second embodiment.

In a preferred embodiment of the alternative process, the mixture of stereoisomeric forms of 6-bromo-α-[2-(dimethylamino)ethyl]-2-methoxy-α-1-naphthalenyl-β-phenyl-3-quinolineethanol is diastereoisomer A.

As the formed salt of (αR,βS)-6-bromo-α-[2-(dimethylamino)ethyl]-2-methoxy-α-1-naphthalenyl-β-phenyl-3-quinolineethanol and chiral 4-hydroxydinaphtho[2,1-d:1',2'-f][1,3,2]dioxaphosphepin 4-oxide or a derivative thereof, in particular (αR,βS)-6-bromo-α-[2-(dimethylamino)ethyl]-2-methoxy-α-1-naphthalenyl-β-phenyl-3-quinolineethanol * (11bS)-4-hydroxydinaphtho[2,1-d:1',2'-f][1,3,2]dioxaphosphepin 4-oxide salt, crystallizes, it can be separated from the reaction mixture by for instance filtration.

When using diastereoisomer A as the mixture of stereoisomeric forms of 6-bromo-α-[2-(dimethylamino)ethyl]-2-methoxy-α-1-naphthalenyl-β-phenyl-3-quinolineethanol, the desired (αS,βR) enantiomer can be isolated from the residual mother liquid by for instance extraction with a suitable solvent. An example of a suitable extraction solvent is for instance toluene and an alkaline aqueous solution, e.g. an aqueous K₂CO₃ solution. The residual amount of the resolution agent in the mother liquid will be retained in the alkaline aqueous layer, whereas the desired (αS,βR) enantiomer will be present in the organic layer. After separating the organic layer from the aqueous layer using techniques well-known to the skilled person, said organic layer can be concentrated to dryness, for instance under vacuum, resulting in the desired (αS,βR) enantiomer.

Alternatively, the (αS,βR) enantiomer can be isolated from the residual mother liquid by applying the process of the first embodiment. The mother liquid is in fact a mixture of stereoisomeric forms wherein the desired (αS,βR) enantiomer is predominantly present compared to the (αR,βS) enantiomer.

The obtained (αS,βR) enantiomer can be further recrystallized in a suitable solvent, e.g. ethanol or toluene, as is described hereinafter.

Synthesis of a mixture of stereoisomeric forms of 6-bromo-α-[2-(dimethylamino)ethyl]-2-methoxy-α-1-naphthalenyl-β-phenyl-3-quinolineethanol A mixture of stereoisomeric forms of 6-bromo-α-[2-(dimethylamino)ethyl]-2-methoxy-α-1-naphthalenyl-β-phenyl-3-quinolineethanol including diastereoisomer A from which the desired enantiomer (αS,βR)-6-bromo-α-[2-(dimethylamino)ethyl]-2-methoxy-α-1-naphthalenyl-β-phenyl-3-quinolineethanol is to be isolated, can be prepared according to the protocol disclosed in WO 2004/011436, which is incorporated herein by reference.

Alternatively, a mixture of stereoisomeric forms of 6-bromo-α-[2-(dimethylamino)ethyl]-2-methoxy-α-1-naphthalenyl-β-phenyl-3-quinolineethanol can also be prepared by reacting 3-benzyl-6-bromo-2-methoxyquinoline with lithium-diisopropylamide and (3-dimethylamino)-1'-propionaphthone in a suitable solvent, such as for example an apolar aprotonic solvent such as an ether, preferably tetrahydrofuran, preferably at reduced temperature, such as a temperature below 0° C., more preferably at −70 to −80° C., followed by adding a suitable acid, such as for example acetic acid.

The thus obtained mixture of stereoisomeric forms of 6-bromo-α-[2-(dimethylamino)ethyl]-2-methoxy-α-1-naphthalenyl-β-phenyl-3-quinolineethanol can optionally be enriched with diastereoisomer A by seeding the reaction mixture with diastereoisomer B, obtained in previous preparation processes according to the present invention or obtained according to the protocol described in WO 2004/011436, in order to promote crystallization of diastereoisomer B followed by filtering off said diastereoisomer B. The resulting mixture of stereoisomeric forms can optionally further be enriched with diastereoisomer A by crystallization from a suitable solvent, such as for example ethanol. Enrichment (or purification) of a reaction mixture with a specific diastereoisomer or enantiomer means that the ratio of that specific diastereoisomer or enantiomer to the other one is increased.

Thus, the present invention also relates to a process for preparing (αS,βR)-6-bromo-α-[2-(dimethylamino)ethyl]-2-methoxy-α-1-naphthalenyl-β-phenyl-3-quinolineethanol, said process comprising a) reacting 3-benzyl-6-bromo-2-methoxyquinoline with lithium-diisopropylamide and (3-dimethylamino)-1'-propionaphthone in a suitable solvent, such as for example an apolar aprotonic solvent such as an ether, preferably tetrahydrofuran, preferably at reduced temperature, such as a temperature below 0° C., followed by adding a suitable acid, such as for example acetic acid; and b) isolating (αS,βR)-6-bromo-α-[2-(dimethylamino)ethyl]-2-methoxy-α-1-naphthalenyl-β-phenyl-3-quinolineethanol from the mixture of stereoisomeric forms of 6-bromo-α-[2-(dimethylamino)ethyl]-2-methoxy-α-1-naphthalenyl-β-phenyl-3-quinolineethanol obtained under a) by using chiral 4-hydroxydinaphtho[2,1-d:1',2'-f][1,3,2]dioxaphosphepin 4-oxide or a derivative thereof, in particular (11bR)-4-hydroxydinaphtho[2,1-d:1',2'-f][1,3,2]dioxaphosphepin 4-oxide, according to the processes as described hereinabove, in particular the first embodiment.

Or in other words, the present invention also relates to a process for isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol according to above-described processes, wherein the mixture of the stereoisomeric forms is obtained by a) reacting 3-benzyl-6-bromo-2-methoxyquinoline with lithium-diisopropylamide and (3-dimethylamino)-1'-propionaphthone in a suitable solvent, such as for example an apolar aprotonic solvent such as an ether, preferably tetrahydrofuran, preferably at reduced temperature, such as a temperature below 0° C., followed by adding a suitable acid, such as for example acetic acid.

The present invention also relates to a process comprising
a) reacting 3-benzyl-6-bromo-2-methoxyquinoline with lithium-diisopropylamide and (3-dimethylamino)-1'-propionaphthone in a suitable solvent, such as for example an apolar aprotonic solvent such as an ether, preferably tetrahydrofuran, preferably at reduced temperature, such as a temperature below 0° C., followed by adding a suitable acid, such as for example acetic acid;
b) enriching (or purifying) the reaction mixture obtained under a) with the racemic mixture of (αS,βR)-6-bromo-α-[2-(dimethylamino)ethyl]-2-methoxy-α-1-naphthalenyl-β-phenyl-3-quinolineethanol and (αR,βS)-6-bromo-α-[2-(dimethylamino)ethyl]-2-methoxy-α-1-naphthalenyl-β-phenyl-3-quinolineethanol, by removing racemic mixture of (αR,βR)-6-bromo-α-[2-(dimethylamino)ethyl]-2-methoxy-α-1-naphthalenyl-β-phenyl-3-quinolineethanol and (αS,βS)-6-bromo-α-[2-(dimethylamino)ethyl]-2-methoxy-α-1-naphthalenyl-β-phenyl-3-quinolineethanol, from the reaction mixture;
c) isolating (αS,βR)-6-bromo-α-[2-(dimethylamino)ethyl]-2-methoxy-α-1-naphthalenyl-β-phenyl-3-quinolineethanol from the mixture of stereoisomeric forms of 6-bromo-α-[2-(dimethylamino)ethyl]-2-methoxy-α-1-naphthalenyl-β-phenyl-3-quinolineethanol obtained under b) by using chiral 4-hydroxydinaphtho[2,1-d:1',2'-f][1,3,2]dioxaphosphepin 4-oxide or a derivative thereof, in particular (11bR)-4-hydroxydinaphtho[2,1-d:1',2'-f][1,3,2]dioxaphosphepin 4-oxide, according to the processes as described hereinabove, in particular the first embodiment.

Or in other words, the present invention also relates to a process for isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol according to above-described processes, wherein the mixture of the stereoisomeric forms is obtained by a) reacting 3-benzyl-6-bromo-2-methoxyquinoline with lithium-diisopropylamide and (3-dimethylamino)-1'-propionaphthone in a suitable solvent, such as for example an apolar aprotonic solvent such as an ether, preferably tetrahydrofuran, preferably at reduced temperature, such as a temperature below 0° C., followed by adding a suitable acid, such as for example acetic acid;
b) enriching (purifying) the mixture obtained under a) with the racemic mixture of (αS,βR)-6-bromo-α-[2-(dimethylamino)ethyl]-2-methoxy-α-1-naphthalenyl-β-phenyl-3-quinolineethanol and (αR,βS)-6-bromo-α-[2-(dimethylamino)ethyl]-2-methoxy-α-1-naphthalenyl-β-phenyl-3-quinolineethanol, by removing racemic mixture of (αS,βS)-6-bromo-α-[2-(dimethylamino)ethyl]-2-methoxy-α-1-naphthalenyl-β-phenyl-3-quinolineethanol and (αR,βR)-6-bromo-α-[2-(dimethylamino)ethyl]-2-methoxy-α-1-naphthalenyl-β-phenyl-3-quinolineethanol from the reaction mixture.

The present invention also relates to a process comprising
a) reacting 3-benzyl-6-bromo-2-methoxyquinoline with lithium-diisopropylamide and (3-dimethylamino)-1'-propionaphthone in a suitable solvent, such as for example an apolar aprotonic solvent such as an ether, preferably tetrahydrofuran, preferably at reduced temperature, such as a temperature below 0° C., followed by adding a suitable acid, such as for example acetic acid;
b) enriching (or purifying) the reaction mixture obtained under a) with the racemic mixture of (αS,βR)-6-bromo-α-[2-(dimethylamino)ethyl]-2-methoxy-α-1-naphthalenyl-β-phenyl-3-quinolineethanol and (αR,βS)-6-bromo-α-[2-(dimethylamino)ethyl]-2-methoxy-α-1-naphthalenyl-β-phenyl-3-quinolineethanol, by removing racemic mixture of (αR,βR)-6-bromo-α-[2-(dimethylamino)ethyl]-2-methoxy-α-1-naphthalenyl-β-phenyl-3-quinolineethanol and (αS,βS)-6-bromo-α-[2-(dimethylamino)ethyl]-2-methoxy-α-1-naphthalenyl-β-phenyl-3-quinolineethanol, from the reaction mixture;
c) crystallizing the resulting stereoisomeric forms of 6-bromo-α-[2-(dimethylamino)ethyl]-2-methoxy-α-1-naphthalenyl-β-phenyl-3-quinolineethanol from the reaction mixture obtained under b) in a suitable solvent, such as for example an alcohol or an ether/alcohol mixture, preferably an alcohol, wherein the alcohol is preferably ethanol and the ether is preferably tetrahydrofuran;
d) isolating (αS,βR)-6-bromo-α-[2-(dimethylamino)ethyl]-2-methoxy-α-1-naphthalenyl-β-phenyl-3-quinolineethanol from the mixture of stereoisomeric forms of 6-bromo-α-[2-(dimethylamino)ethyl]-2-methoxy-α-1-naphthalenyl-β-phenyl-3-quinolineethanol obtained under c) by using chiral 4-hydroxydinaphtho[2,1-d:1',2'-f][1,3,2]dioxaphosphepin 4-oxide or a derivative thereof, in particular (11bR)-4-hydroxydinaphtho[2,1-d:1',2'-f][1,3,2]dioxaphosphepin 4-oxide, according to the processes as described hereinabove, in particular the first embodiment.

Or in other words, the present invention also relates to a process for isolating (αS,βR)-6-bromo-α-[2-(dimethylamino)ethyl]-2-methoxy-α-1-naphthalenyl-β-phenyl-3-quinolineethanol from a mixture of stereoisomeric forms of 6-bromo-α-[2-(dimethylamino)ethyl]-2-methoxy-α-1-naphthalenyl-β-phenyl-3-quinolineethanol according to above-described processes, wherein the mixture of the stereoisomeric forms is obtained by a) reacting 3-benzyl-6-bromo-2-methoxyquinoline with lithium-diisopropylamide and (3-dimethylamino)-1'-propionaphthone in a suitable solvent, such as for example an apolar aprotonic solvent such as an ether, preferably tetrahydrofuran, preferably at reduced temperature, such as a temperature below 0° C., followed by adding a suitable acid, such as for example acetic acid;
b) enriching (purifying) the mixture obtained under a) with the racemic mixture of (αS,βR)-6-bromo-α-[2-(dimethylamino)ethyl]-2-methoxy-α-1-naphthalenyl-β-phenyl-3-quinolineethanol and (αR,βS)-6-bromo-α-[2-(dimethylamino)ethyl]-2-methoxy-α-1-naphthalenyl-β-phenyl-3-quinolineethanol, by removing racemic mixture of (αS,βS)-6-bromo-α-[2-(dimethylamino)ethyl]-2-methoxy-α-1-naphthalenyl-β-phenyl-3-quinolineethanol and (αR,βR)-6-bromo-α-[2-(dimethylamino)ethyl]-2-methoxy-α-1-naphthalenyl-β-phenyl-3-quinolineethanol from the reaction mixture; and c) crystallizing the resulting stereoisomeric forms of 6-bromo-α-[2-(dimethylamino)ethyl]-2-methoxy-α-1-naphthalenyl-β-phenyl-3-quinolineethanol from the reaction mixture obtained under b) in a suitable solvent.

EXPERIMENTAL PART

A. Preparation of a mixture of stereoisomeric forms of 6-bromo-α-[2-(dimethylamino)ethyl]-2-methoxy-α-1-naphthalenyl-β-phenyl-3-quinolineethanol

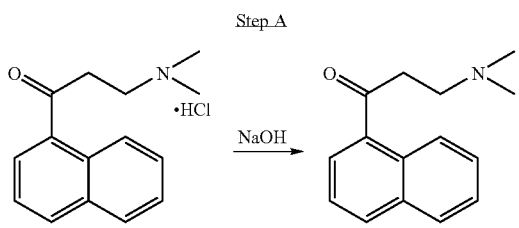

(3-dimethylamino)-1'-propionaphthone-HCl (48.47 g; 183.8 mmol) was dissolved in water (157.5 g) and stirred for 5 to 10 minutes at room temperature. Sodium hydroxide (51.46 g; 386 mmol) was added as a 30% solution in water and the reaction mixture was stirred for 10 to 15 minutes. Toluene (105 g) was added and the mixture was stirred for 10 to 15 minutes followed by separation of the layers. To the organic layer, water (100 g) was added and stirring was continued for 10 to 15 minutes, followed by separation of the layers. The organic layer was concentrated in vacuo at 50 to 60° C., yielding 98.2% of (3-dimethylamino)-1'-propionaphthone.

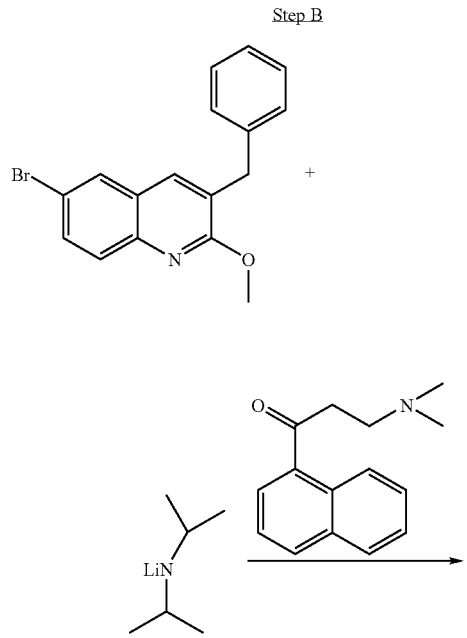

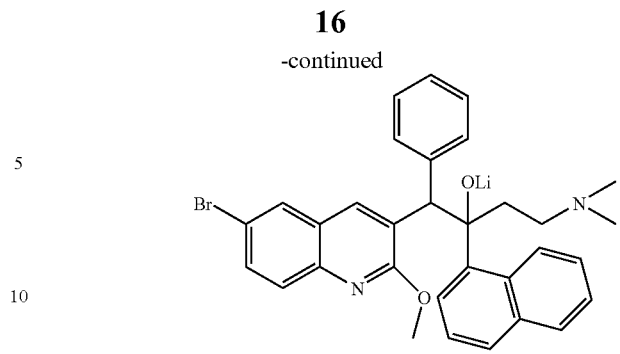

To tetrahydrofuran (74 g) was added lithium diisopropylamide (92.4 g; 228 mmol) as a 25% solution in tetrahydrofuran, heptane and ethylbenzene under $N_2$ atmosphere at 20 to 25° C. The solution was cooled to −70 to −80° C. and 3-benzyl-6-bromo-2-methoxyquinoline (57.4 g; 175 mmol) in tetrahydrofuran (74 g) was added dropwise during 90 minutes (80 to 150 minutes). The reaction mixture was stirred for 90 minutes (80-150 minutes) at −70 to −80° C.

A solution of (3-dimethylamino)-1'-propionaphthone (45.7 g; 175 mmol; prepared according to step A) in tetrahydrofuran (74 g) was added dropwise to the reaction mixture during 90 minutes (80-150 minutes) at −70 to −80° C. The reaction mixture was stirred at −70 to −80° C. for 14 hours (8 to 15 hours).

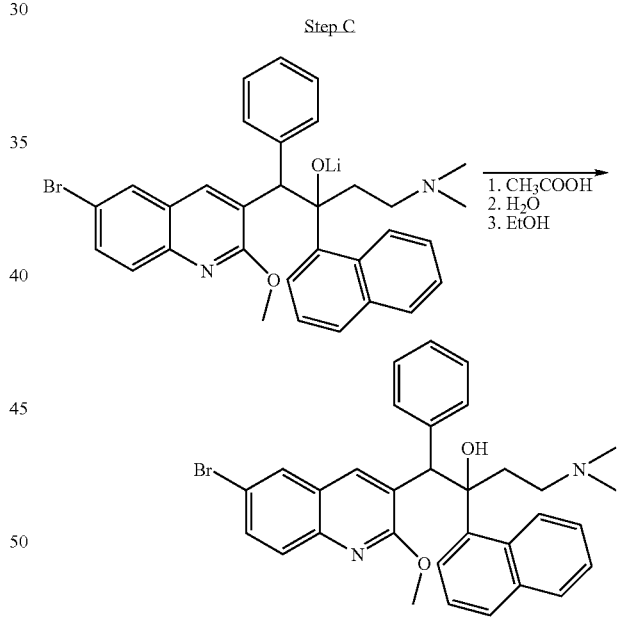

The reaction mixture obtained in Step B was added to a precooled (−10° C.) solution of acetic acid (39 g; 438 mmol) in tetrahydrofuran (39 g) during 10 to 30 minutes. 15 minutes after completing the addition, the mixture was seeded with diastereoisomer B (0.05 g; 0.1 mmol) obtained from previous preparation processes and the reaction mixture was stirred for 6 hours (5 to 7 hours) at 0 to 5° C. Water (200 g) was added dropwise during 5 to 30 minutes and the reaction mixture was stirred for 30 to 40 minutes at 0 to 5° C. Diastereoisomer B was filtered off and washed twice with tetrahydrofuran (30 g for each wash step). The two layers were separated.

The organic mother layer was concentrated in vacuo at 50 to 55° C. Ethanol (250 g) was added and the reaction mixture was further concentrated in vacuo at 50 to 60° C. The mixture was cooled during 0.5 to 1.5 hours to 0° C. (−5 to 5° C.) and stirred for 1 to 2 hours at this temperature followed by filtration. The filter residue was washed twice with ethanol (50 g for each wash step) and the obtained product was dried at 80° C. (75 to 85° C.) in vacuo. Yield: 37.48 g of a solid containing 82.7% (w/w) of diastereoisomer A and 7.7% (w/w) of diastereoisomer B.

B. Isolation of the specific enantiomer (αS,βR)-6-bromo-α-[2-(dimethylamino)ethyl]-2-methoxy-α-1-naphthalenyl-β-phenyl-3-quinolineethanol from a mixture of stereoisomeric forms by using (11bR)-4-hydroxydinaphtho[2,1-d:1',2'-f][1,3,2]dioxaphosphepin 4-oxide The solid obtained under step C (30.45 g; 50 mmol; 1 eq.) was suspended in acetone (193.3 g) at a temperature of 20 to 30° C. This suspension was seeded with (αS,βR)-6-bromo-α-[2-(dimethylamino)ethyl]-2-methoxy-α-1-naphthalenyl-β-phenyl-3-quinolineethanol * (11bR)-4-hydroxydinaphtho[2,1-d:1',2'-f][1,3,2]dioxaphosphepin 4-oxide salt (9 mg; 0.016 mmol) obtained from previous preparation processes. (11bR)-4-hydroxydinaphtho[2,1-d:1',2'-f][1,3,2]dioxaphosphepin 4-oxide (17.60 g; 50 mmol; 1 eq.) was dissolved in dimethylsulfoxide (38.7 g) at 40 to 50° C. and this solution was added via a filter to the above suspension in acetone within a time frame of 5 to 15 minutes. Then, the reaction mixture was seeded again with (αS,βR)6-bromo-α-[2-(dimethylamino)ethyl]-2-methoxy-α-(1-naphthyl)-β-phenyl-3-quinolineethanol * (11bR)-4-hydroxydinaphtho[2,1-d:1',2'-f][1,3,2]dioxaphosphepin 4-oxide salt (9 mg; 0.016 mmol) obtained from previous preparation processes.

The resulting suspension was stirred for 60 minutes (45 to 75 minutes), followed by heating to reflux. The suspension was stirred for 60 minutes (45 to 75 minutes) under reflux, followed by cooling to 25° C. (20 to 30° C.) in 30 to 60 minutes and stirring for 1 to 2 hours at 20 to 30° C. The resulting solid was filtered off and washed twice with acetone (62.5 g for each wash step). The resulting residue (59 g) was suspended in acetone (185.4 g) and the suspension was heated to reflux and stirred under reflux for 2 hours (1.5 to 2.5 hours) followed by cooling to 25° C. (20 to 30° C.) in 30 to 45 minutes and stirring for 45 to 75 minutes. The resulting solid was filtered off and washed with acetone (47 g) followed by washing with toluene (55 g).

The obtained solid (54.96 g) was suspended in toluene (40.3 g) and treated (1.4 eq.) with a 10% potassium carbonate solution (4.23 g K$_2$CO$_3$ in 38.02 g of purified water). The mixture was heated to 80-85° C. and the aqueous layer was separated.

To the organic layer, a potassium carbonate solution (0.4 eq.) (1.23 g of K$_2$CO$_3$ in 11.07 g of purified water) was added. After stirring for 5 to 15 minutes, the aqueous layer was separated and the organic layer was washed with purified water (11.8 g) at 80 to 85° C.

The organic layer was concentrated at 55° C. (50 to 60° C.) under vacuum.

The residue was treated with ethanol (69 g) at a temperature 45 to 50° C. followed by cooling within 0.5 to 1.5 hours to 0 to 5° C. and stirring for 0.5 to 1 hour at this temperature. The resulting solid was filtered off, washed twice with ethanol (18 g for each wash step) and dried in vacuo at 70° C. (65 to 75° C.). Yield: 39% by weight (or 78% by weight calculated on the desired enantiomer) of (αS,βR)-6-bromo-α-[2-(dimethylamino)ethyl]-2-methoxy-α-1-naphthalenyl-β-phenyl-3-quinolineethanol (HPLC purity: >99.6%; enantiomeric excess >99.8%, m.p. 182-184° C.).

Purity was determined by HPLC using a YMC-Pack ODS-AQ (150×4.6 mm, 3 μm) column using as Mobile phase: Mobile phase A: water/trifluoroacetic acid (1000 ml/1 ml); Mobile phase B; acetonitrile/trifluoroacetic acid (1000 ml/0.8 ml); eluent gradient starting with 75% of A and 25% of B→10% of A and 90% of B.

Enantiomeric excess was determined by HPLC using a Cyclobond I RSP (250×4.6 mm) column using as mobile phase: MeOH/Water/Ammonium acetate (60 ml/40 ml/0.154 g) adjusted to pH 7 with acetic acid.

The obtained product (19.0 g) was suspended in toluene (10.96 g) and heated to 90° C. The mixture was filtered in the heat and the filter was washed with toluene (1.5 g). The solution was cooled to 70° C. and ethanol (22.16 g) was added dropwise. During the addition of ethanol, the product started to crystallize (optionally a few mg of (αS,βR)6-bromo-α-[2-(dimethylamino)ethyl]-2-methoxy-α-(1-naphthyl)-β-phenyl-3-quinolineethanol may be added). A further ethanol (32.31 g) was added dropwise at 65° C. and the suspension was cooled to 0° C. and stirred for 1 hour. The residue was filtered off and washed with ethanol in 2 parts (52 g). The resulting product was dried (40 to 70° C.), yielding 17.07 g of (αS,βR)-6-bromo-α-[2-(dimethylamino)ethyl]-2-methoxy-α-1-naphthalenyl-β-phenyl-3-quinolineethanol.

The invention claimed is:
1. A salt of (αS,βR)-6-bromo-α-[2-(dimethylamino)ethyl]-2-methoxy-α-1-naphthalenyl-β-phenyl-3-quinolineethanol and (11bR)-4-hydroxydinaphtho[2,1-d:1',2'-f][1,3,2]dioxaphosphepin 4-oxide.

\* \* \* \* \*